United States Patent
Sekiguchi et al.

(10) Patent No.: US 7,684,044 B2
(45) Date of Patent: Mar. 23, 2010

(54) SENSOR DEVICE

(75) Inventors: Ryota Sekiguchi, Kawasaki (JP); Yoichiro Handa, Yokohama (JP); Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 595 days.

(21) Appl. No.: 11/596,854

(22) PCT Filed: Aug. 31, 2006

(86) PCT No.: PCT/JP2006/017697

§ 371 (c)(1),
(2), (4) Date: Nov. 17, 2006

(87) PCT Pub. No.: WO2007/029758

PCT Pub. Date: Mar. 15, 2007

(65) Prior Publication Data

US 2008/0273207 A1    Nov. 6, 2008

(30) Foreign Application Priority Data

Sep. 5, 2005   (JP) ............................. 2005-256654

(51) Int. Cl.
*G01N 21/55*   (2006.01)
(52) U.S. Cl. ................................... 356/445
(58) Field of Classification Search ............ None
See application file for complete search history.

(56) References Cited

U.S. PATENT DOCUMENTS

| | | | | |
|---|---|---|---|---|
| 5,858,799 A * | 1/1999 | Yee et al. | ........... | 356/445 |
| 6,421,128 B1 | 7/2002 | Salamon et al. | ........... | 356/445 |
| 6,570,158 B2 | 5/2003 | Feygin | ........... | 250/332 |
| 6,738,141 B1 | 5/2004 | Thirstrup | ........... | 356/445 |
| 6,782,179 B2 * | 8/2004 | Bozhevolnyi et al. | ........... | 356/445 |
| 7,015,471 B2 | 3/2006 | Franzen et al. | ........... | 250/338.1 |
| 7,033,542 B2 | 4/2006 | Archibald et al. | ........... | 422/82.09 |
| 2001/0040130 A1 * | 11/2001 | Lorch et al. | ........... | 210/601 |
| 2003/0175160 A1 * | 9/2003 | Archibald et al. | ........... | 422/82.05 |
| 2004/0113077 A1 * | 6/2004 | Franzen et al. | ........... | 250/338.1 |
| 2006/0231762 A1 | 10/2006 | Ohtake et al. | ........... | 250/341.8 |

FOREIGN PATENT DOCUMENTS

| | | |
|---|---|---|
| EP | 1 630 542 | 3/2006 |
| JP | 2004-354246 | 12/2004 |
| WO | 99/05509 | 2/1999 |

OTHER PUBLICATIONS

Charles Kittel, "Introduction to Solid State Physics", Seventh Edition, John Wiley & Sons, Inc., 1996, pp. 220-221.
Jiři Homola, et al., "Surface plasmon resonance sensors: review", Sensors and Actuators B, vol. 54, 1999, pp. 3-15.

* cited by examiner

*Primary Examiner*—Gregory J. Toatley, Jr.
*Assistant Examiner*—Juan D Valentin
(74) *Attorney, Agent, or Firm*—Fitzpatrick, Cella, Harper & Scinto

(57) ABSTRACT

It has been requested to enhance sensitivity of a surface plasmon resonance sensor in a frequency region from a millimeter wave band to a terahertz band, from 30 GHz to 30 THz. Then, the present invention provides a sensor whose sensitivity is further improved by an analyte holding portion being equipped with a semiconductor and a medium.

17 Claims, 4 Drawing Sheets

SENSOR DEVICE

TECHNICAL FIELD

The present invention relates to a sensor device in a frequency region from 30 GHz to 30 THz, or from a millimeter wave band to a terahertz band.

BACKGROUND ART

A sensor using surface plasmon resonance has been known as highly sensitive measuring means of a trace analyte and optical property of an analyte until now.

A typical surface plasmon resonance sensor makes a metal thin film, provided in an end face of an ATR prism coupler, generate surface plasmon in resonance to measure the optical properties of the analyte disposed in the vicinity of it with high sensitivity. Since it is possible to read unique information of an analyte in optical properties such as a refractive index, absorption, and a fluorescent characteristic, it is also possible to apply a surface plasmon resonance sensor also as a biosensor.

It is described in Jiri Homola, et al., Sensors and Actuators B, Vol. 54, 3 (1999) that sensitivity of a surface plasmon resonance sensor is excellent in a visible region. For example, in angular interrogation of a typical sensor device using an ATR prism coupler (BK7 glass as an ATR prism coupler medium, 50 nm gold as a metal thin film, and 1.32 of refractive index of an analyte), sensitivity $S(p\theta)$ defined by a refractive index change and a resonance condition change of the analyte shows a value of 100 to 200 [deg/RIU]. Assuming an angular resolution of a typical system ($1\times10^{-4}$ [deg]), this value means that it is possible to measure even such an extremely minute change that a refractive index change of the analyte is $5\times10^{-7}$ to $1\times10^{-6}$ [RIU]. On the other hand, recently, it has being known that features of optical properties of sugar, protein, and the like exist also in a frequency region from a millimeter wave band to a terahertz band, and importance of applying a surface plasmon resonance sensor in a visible region to a frequency region from a millimeter wave band to a terahertz band is high. However, according to Jiri Homola, et al., Sensors and Actuators B, Vol. 54, 16 (1999), it is described that the sensitivity $S(p\theta)$ drops with a longer wavelength of an electromagnetic wave to be used.

In addition, although Japanese Patent Application Laid-Open No. 2004-354246 discloses a sensor device using a prism in a terahertz band, it does not become highly sensitive measuring means of optical properties of an analyte since an electric field enhancing effect generated at the time of surface plasmon resonance is not obtained because of nonresonant structure.

Hence, also in the frequency region from 30 GHz to 30 THz, or from a millimeter wave band to a terahertz band, a sensor which has the sensitivity to the extent currently used in a visible region has been requested.

The present invention aims at providing a surface plasmon resonance sensor in the frequency region from a millimeter wave band to a terahertz band, from 30 GHz to 30 THz which solves the above-mentioned tasks and has sensitivity comparable to a surface plasmon resonance sensor in a visible region.

DISCLOSURE OF THE INVENTION

According to an aspect of the present invention, there is provided a sensor device comprising:

an analyte holding portion for locating an analyte;

a radiation means for radiating an electromagnetic wave which includes a part of a frequency region from 30 GHz to 30 THz toward the analyte holding portion; and a detection means for detecting the electromagnetic wave reflected from the analyte holding portion, the analyte holding portion comprising a semiconductor and a medium, a real part of a dielectric constant of the semiconductor being negative, the square of a refractive index of the medium being smaller than the real part of the dielectric constant, the analyte opposing the medium via the semiconductor when detecting the analyte.

According to another aspect of the present invention, there is provided a sensor device comprising:

an analyte holding portion for locating an analyte;

a radiation means for radiating an electromagnetic wave which includes a part of a frequency region from 30 GHz to 30 THz toward the analyte holding portion; and a detection means for detecting the electromagnetic wave reflected from the analyte holding portion, the analyte holding portion comprising a semiconductor and a medium, a real part of a dielectric constant of the semiconductor being negative, the square of a refractive index of the medium being smaller than the real part of the dielectric constant, the analyte being located between the semiconductor and the medium when detecting the analyte.

The analyte holding portion preferably comprises an electrode.

The electrode is preferably a means of applying an electric field to the semiconductor.

The sensor device preferably comprises a light radiation means for radiating light on the semiconductor.

The sensor device preferably comprises an incident angle change means for changing an incident angle of an electromagnetic wave which includes a part of a frequency region from 30 GHz to 30 THz to the analyte holding portion.

The semiconductor is preferably selected from the group consisting of InAs, GaAs, InSb and InN.

The analyte holding portion is preferably coated with a gold film 5 nm or less in thickness so as to improve an adsorptiveness of an analyte.

According to a still another aspect of the present invention, there is provided a sensor device comprising:

an analyte holding portion for locating an analyte;

a radiation means for radiating an electromagnetic wave which includes a part of a frequency region from 30 GHz to 30 THz toward the analyte holding portion; and a detection means for detecting the electromagnetic wave reflected from the analyte holding portion, the analyte holding portion comprising a first layer and a second layer, the first layer and second layer satisfying the following formula:

$$Re(\in_1) < -n_2^2$$

where $Re(\in_1)$ is a real part of a dielectric constant of the first layer, and $n_2$ is a refractive index of the second layer.

By taking the structure of the present invention, it becomes possible to provide the sensor whose sensitivity in the frequency region of 30 GHz to 30 THz is improved.

BEST MODE FOR CARRYING OUT THE INVENTION (Constitution)

Figure 1:
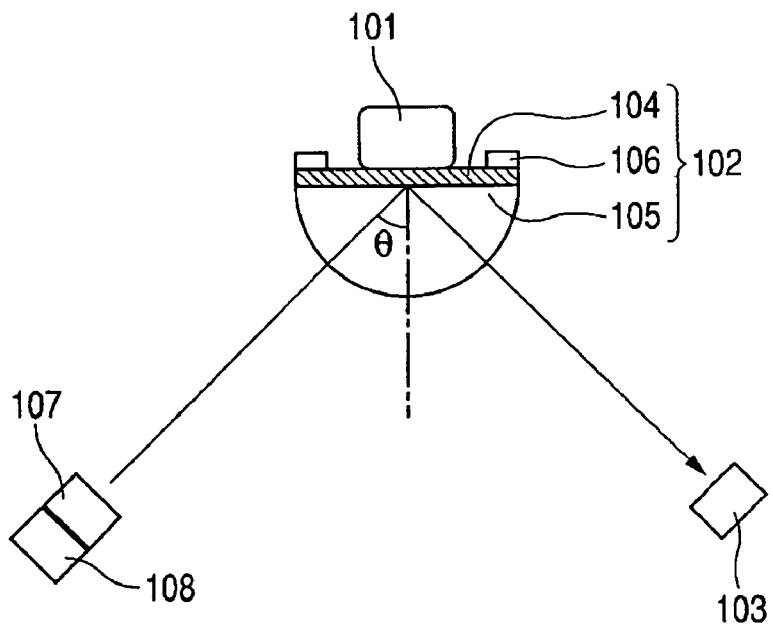
FIG. 1 is a sectional view showing structure of a sensor device according to this embodiment.

As for the present invention, specific structure of a sensor device will be explained using FIG. 1. FIG. 1 shows the structure of the sensor device of a first embodiment in the present invention, and is a sectional view of the sensor device.

The sensor device comprises an analyte holding portion 102 and a detection means 103, and the analyte holding portion is equipped with a semiconductor 104 and a medium 105. In FIG. 1, it further comprises electrodes 106. An analyte 101 is located in a position of facing the medium 105 through the semiconductor 104.

An analyte is detected by radiating an electromagnetic wave from electromagnetic wave radiation means 107 of radiating the electromagnetic wave including a part of a frequency band domain from 30 GHz to 30 THz, or from a millimeter wave band to a terahertz band, in a state that the analyte is located near the analyte holding portion. Depending on a method of measurement, it is preferable to provide angle change means 108 for changing an incident angle θ.

The detection means is for detecting amplitude or strength of a reflected electromagnetic wave, and may use a well known detector such as a bolometer, a pyro, a Schottky diode, or the like. The amplitude or strength of the electromagnetic wave which are acquired are used in the measurement described later.

Alternatively, the analyte holding portion comprises a first layer and a second layer, and may just satisfy the following formula.

$$Re(\in_1) < -n_2^2$$

where, $Re(\in_1)$ denotes a real part of a dielectric constant of the first layer, and $n_2$ denotes a refractive index of the second layer. The above formula is a relational expression required for surface plasmon being held in the first layer in the analyte holding portion, relation between the semiconductor 104 and medium has high possibility of satisfying the above formula from 30 GHz to 30 THz, or from a millimeter wave band to a terahertz band, and in the case of FIG. 1, the first layer is equivalent to the semiconductor 104 and the second layer is equivalent to the medium 105. To speak intelligibly, the equation means a state that the real part of dielectric constant of the semiconductor is negative, and, the square of refractive index of the medium is smaller than the real part of dielectric constant of the semiconductor.

As the semiconductor 104, what shows a metallic effect in a frequency region of a millimeter wave band to a terahertz band is adequate, and it is possible to use a carrier-doped semiconductor or an undoped semiconductor. What shows a coupling effect of an electromagnetic wave and surface plasmon using Attenuated Total Reflection of an electromagnetic wave is adequate as the medium, and it is simplest to use an ATR prism coupler. So long as the medium has a shape which has an end face, what kind of shape may be sufficient essentially. In addition, in order to expect sufficient electromagnetic wave coupling between the medium and semiconductor, it is required to locate the semiconductor within attenuation length of an evanescent wave which localizes on the end face of the medium. Preferably, the semiconductor is provided within a distance that a distance from the end face of the medium is equal to or less than a wavelength of an electromagnetic wave which is used.

Furthermore, although the analyte holding portion may have the electrodes 106, the electrodes 106 are for applying an electric field to the semiconductor and controlling carrier density in the semiconductor. So long as an electric field can be applied, what kind of thing may be used and gold, platinum, palladium, copper, aluminum, tungsten, or the like may be sufficient. Alternatively, in order to modulate the carrier density in the semiconductor, optical radiation is also conceivable, and it is sufficient to use a laser, an LED, or the like, which has larger photon energy than a band gap of a semiconductor, for optical radiation at this time.

(Principle)

In the present invention, a principle which enables enhancement in sensitivity of the sensor when making a frequency of an electromagnetic wave in a frequency region of a millimeter wave band to a terahertz band will be explained.

Figure 2:
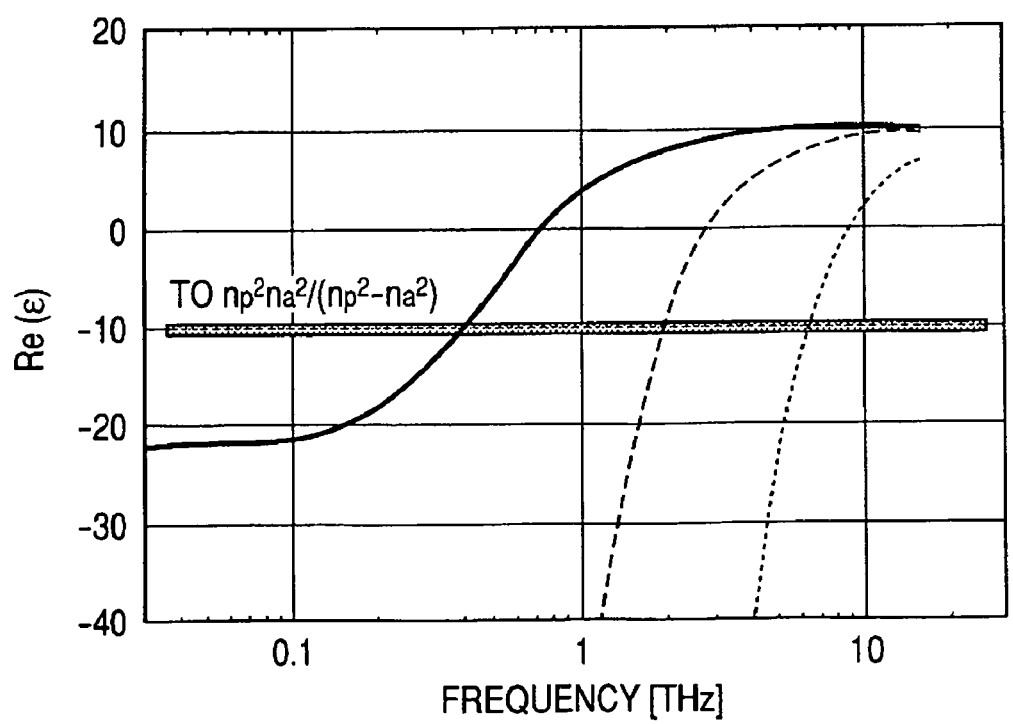
FIG. 2 is a graph showing dispersion by a semiconductor in the sensor device according to the present invention.

FIG. 1 shows structure of a sensor device which is used. Sensitivity $S(p\theta)$ of a sensor device depends on a state of surface plasmon, and in particular, is strongly governed by a real part $Re(\in)$ of a dielectric constant of a semiconductor holding the surface plasmon. As shown in Jiri Homola, et al., Sensors and Actuators B, Vol. 54, 16 (1999), when a refractive index $n_p$ of an ATR prism coupler medium and an effectual refractive index $n_a$ of an analyte take $|Re(\in)|=n_p^2 n_a^2/(n_p^2-n_a^2)$, sensitivity $S(p\theta)$ becomes maximum. A real part of a dielectric constant of typical metal in a visible region is a value of $Re(\in) \approx -10$, this is equal to the order at the time of $n_p \approx 1.5$ and $n_a \approx 1.3$ as reference values of a typical ATR prism coupler medium and an analyte. However, it is known that a real part of a dielectric constant of metal in a frequency region of a millimeter wave band to a terahertz band is $-10^6 \leq Re(\in) \leq -10^5$. On the other hand, a real part of a dielectric constant of a semiconductor is governed by variable free carrier density by carrier doping, and according to a Drude's equation, it can be expressed as $Re(\in)=\in_b-\omega_p^2/(\omega^2+\gamma^2)$ Nevertheless, $\in_b$ denotes a background dielectric constant and $\gamma^{-1}$ denotes a relaxation time. It is known that it is possible to write a plasma frequency $\omega_p$ as $\omega_p=\sqrt{(N \cdot e^2/m_{eff}\in_0)}$ with free carrier density N, effective mass $m_{eff}$, and a dielectric constant in a vacuum $\in_0$. The "e" denotes an elementary charge. Now, assuming a typical semiconductor has 0.1 of carrier effective mass, 2 [psec] of relaxation time, and 10 of background dielectric constant, and when a Drude dispersion is shown with making carrier density a parameter, it becomes as shown in FIG. 2. In FIG. 2, carrier density shown by a continuous line is $1 \times 10^{16}$ [cm$^{-3}$], carrier density shown by a broken line $1 \times 10^{17}$ [cm$^{-3}$], and carrier density shown by a dotted line is $1 \times 10^{18}$ [cm$^{-3}$]. According to FIG. 2, it turns out that it is possible to select a value of $n_p^2 n_a^2/(n_p^2-n_a^2)$, which is suitable for enhancement in sensitivity of the sensor in comparison with metal, in the frequency region of a millimeter wave band value to a terahertz band as the real part of a dielectric constant of a semiconductor. Hence, a semiconductor applicable to the present invention is a semiconductor whose free carrier density is adjusted in $10^{15}$ [cm$^{-3}$]≦N≦$10^{19}$ [cm$^{-3}$], and these can be obtained by undoping or typical carrier doping. For the frequency region in this, the range of frequency region from 0.1 THz to 10 THz is suitable.

(Detection Method of Analyte)

Although the above description is the explanation of the specific structure and specific principle, a detection method of an analyte will be explained as (1) angular interrogation, and (2) carrier density interrogation, here.

(1) Angular Interrogation

Generally, in a surface plasmon resonance sensor, a measuring method called an angular interrogation is well known as a detection method of an analyte. That is, when an incident wave does not resonate with surface plasmon, which is held by a semiconductor, by an incident angle of the incident wave being controlled, the incident wave causes total reflection to be detected by detection means in a sensor device. Since energy of the incident wave is taken away by surface plasmon when the incident wave resonates, it is not detected by the detection means. A method of using such a sensing operation is the angular interrogation. Further, since a state of surface plasmon held by a semiconductor also changes when an optical property of the analyte changes for a certain reason, a resonance condition also changes. Sensor sensitivity S(pθ) at this time is defined by an incident angle (resonance condition) variation to a refractive index variation of the analyte, and it is possible to evaluate a change of a refractive index of the analyte quantitatively.

In the angular interrogation, sensitivity S(pθ) is important especially, and when the sensitivity S(pθ) is excellent, it becomes possible to measure a minute change of the optical property of the analyte. In the present invention, since it is possible to perform carrier doping of a semiconductor according to a wavelength of an electromagnetic wave to be used, it is possible to improve the sensitivity S(pθ).

(2) Carrier Density Interrogation

Furthermore, in the present invention, an operation of a sensor different from that of a conventional surface plasmon resonance sensor is also possible. That is, it is a method of changing the resonance condition of the incident wave with the surface plasmon held by the semiconductor by changing free carrier density in the semiconductor. Let this be called a carrier density interrogation. Generally, it is possible to modulate free carrier density in a semiconductor by controlling a depletion layer by electric field application, or optically radiating light whose photon energy is larger than a band gap of the semiconductor to be used although it is comparatively short time, and for example, it is possible to expect a sensing operation which is different from the past with the following structure. For example, several electrodes which can perform the above-mentioned electric field application are added to a part of the semiconductor. As a sensing operation at this time, when an incident wave does not resonate with the surface plasmon held by the semiconductor by the free carrier density of the semiconductor being changed by electric field application, the incident wave causes total reflection to be detected by the detection means of the sensor device. Since energy of the incident wave is taken away by the surface plasmon when the incident wave resonates, it is not detected by the detection means. A method of using such a sensing operation is the carrier density interrogation. Of course, it is also possible to perform the same sensing operation by optical radiation. Furthermore, also in the carrier density interrogation, it is possible to perform a quantitative evaluation of the optical property of the analyte by a method according to the angular interrogation.

(Measurement Results of Analyte)

Here, measurement results obtained in (1) angular interrogation and (2) carrier density interrogation will be explained.

(1) Result of Angular Interrogation

Figure 3:
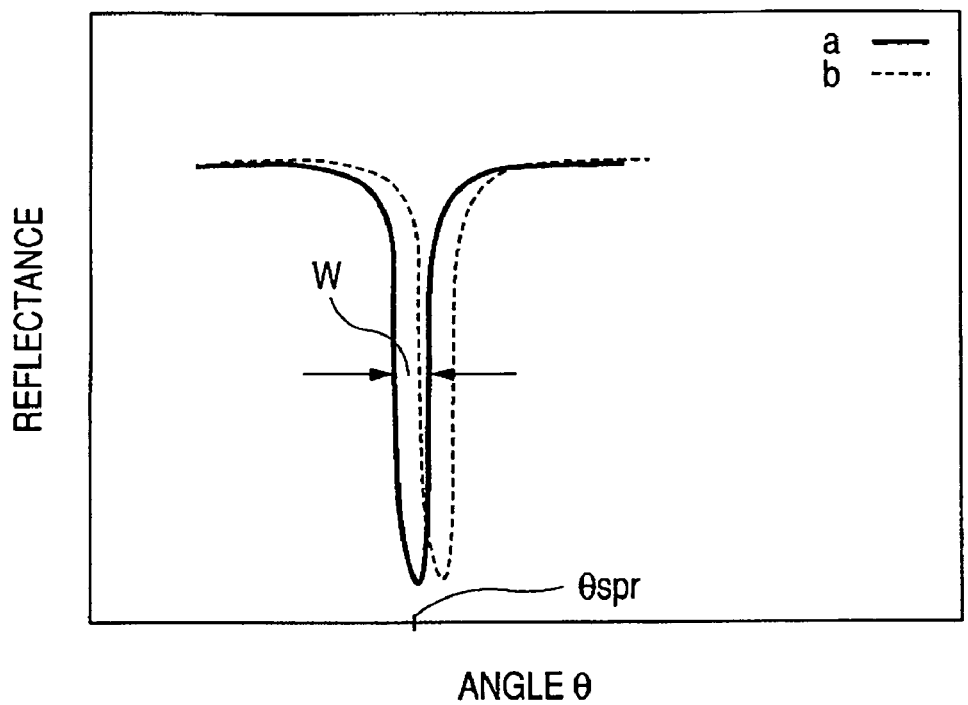
FIG. 3 is a graph showing result of angular interrogation according to this embodiment.

FIG. 3 shows result of the angular interrogation of the sensor device in this embodiment. The graph shows relation between the strength of a reflected wave, which passed through an end face of an ATR prism coupler 105 near a semiconductor 104 in FIG. 1, and the incident angle θ. A dip in resonance condition $\theta_{spr}$ shows that the incident wave and surface plasmon which is held by the semiconductor 104 resonate, and in particular, when a p-polarized light component is included in the incident wave (preferably p-polarized light), reflective strength becomes to the minimum. When a certain minute change occurs in the refractive index of the analyte, the resonance condition $\theta_{spr}$ shifts by S(pθ)Δ$n_a$ expressed by product of the sensitivity S(pθ) and a minute change Δ$n_a$ of the refractive index of the analyte. A curve a in FIG. 3 shows the relation before the minute change of the refractive index of the analyte occurs, and a curve b shows the relation after the minute change of the refractive index occurs. The larger the shift is, the easier detection is, that is, the larger the sensitivity S(pθ) is, the easier the detection of such a minute change Ana of the refractive index is. As already described, since it is possible to improve the sensitivity S(pθ) in the present invention, it is possible to detect the more minute change Δ$n_a$ of the refractive index. At this time, it is desirable for resonant width W in FIG. 3 to be narrower. According to analogy with a surface plasmon resonance sensor in a visible region, it is possible to make resonant width narrower by using a material whose ratio |Re(∈)|/Im(∈) of a real part of a complex dielectric constant ∈ of the semiconductor to be used to an imaginary part is larger. According to a Drude's equation, since Im(∈) is in inverse proportion to a relaxation time $\gamma^{-1}$ of the semiconductor to be used, the larger a relaxation time $\gamma^{-1}$ is, the smaller Im(∈) is. Hence, a material with large mobility is preferable, and for example, it is desirable to select a material, such as InAs or GaAs (See C. Kittel "Introduction to Solid State Physics", 7th edition, John Wiley & Sons Inc.). Recently, since antimony-based materials, such as InSb whose mobility is further higher, also become easily available, it is preferable. In addition, since a material whose mobility is comparatively high in spite of large effective mass also has comparatively large relaxation time $\gamma^{-1}$, nitride-based InN is also preferable.

(2) Result of Carrier Density Interrogation

Figure 4:
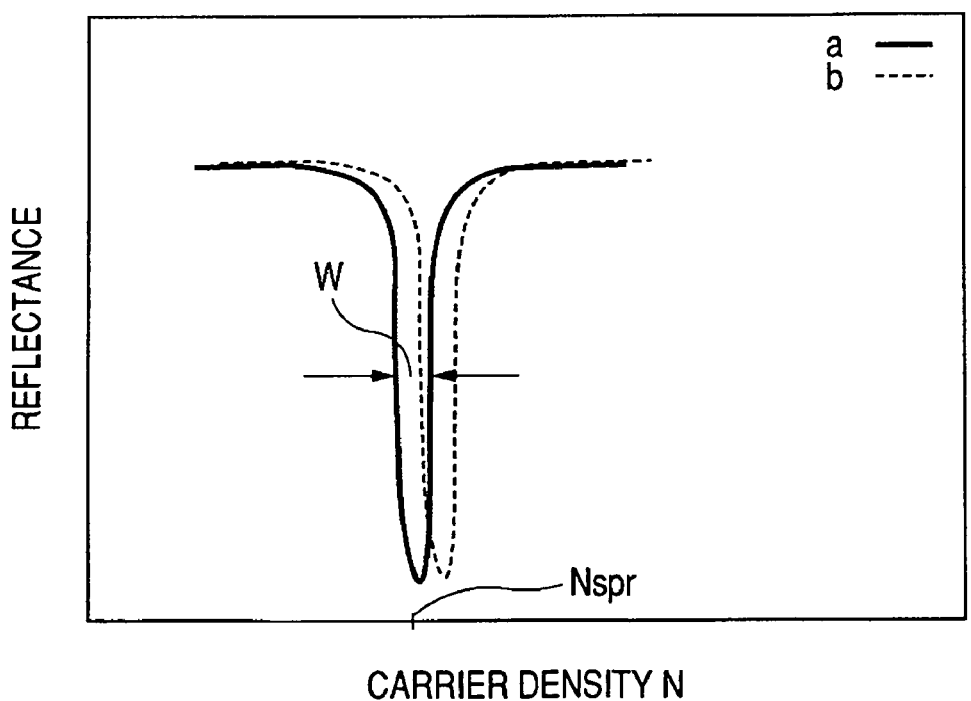
FIG. 4 is a graph showing result of carrier density interrogation according to this embodiment.

FIG. 4 shows result of the carrier density interrogation of the sensor device in this embodiment. The graph shows relation between the strength of a reflected wave, which passed through the end face of the ATR prism coupler 105 near the semiconductor 104 in FIG. 1, and the carrier density in the semiconductor. Here, when modulation means of the carrier density is electric field application, the horizontal axis of the graph may be read as field strength, or when modulation means of the carrier density is optical radiation, the horizontal axis of the graph may be read as optical strength. A dip in resonance condition $N_{spr}$ denotes that the incident wave and surface plasmon which is held by a semiconductor film 204 resonate, and in particular, when a p-polarized light component is included in the incident wave (preferably p-polarized light), reflective strength becomes to the minimum. When a certain minute change occurs in the refractive index of the analyte, the resonance condition $N_{spr}$ is shifted, and in particular, a shift amount becomes large when a material with a large Drude dispersion is used. A curve a in FIG. 4 shows the relation before the minute change of the refractive index of the analyte occurs, and a curve b shows the relation after the minute change of the refractive index occurs.

(Optional Functions)

In addition to the present invention shown above, it is also possible to take the following structures according to objects.

1. Structure that a semiconductor has a coating layer aiming at corrosion control of the semiconductor when an analyte is corrosive to the semiconductor.

2. Structure that a semiconductor has a coating layer aiming at enhancement in adsorption power or holding power when the adsorption power and holding power of an analyte to the semiconductor are small.

3. Structure that a semiconductor has a coating layer aiming at adsorbing or holding selectively only a specific substance to be measured when a plurality of substances are included in an analyte.

4. Structure of including a guide (pass) aiming at an analyte being guided near a semiconductor when the analyte is liquid or a gaseous substance.

5. Structure of including a sealing member aiming at not spilling out an analyte from near a semiconductor when evaporativity or sublimability of the analyte is high.

Nevertheless, when the above-mentioned coating layer, guide (pass), or sealing member is located between the analyte and semiconductor, at least a part of a shape must be thinner than a wavelength to be used. Furthermore, it is desirable that it is a material highly transparent to the wavelength to be used.

In addition, an ATR prism coupler medium needs to be a medium with a larger refractive index than the refractive index of the analyte. Nevertheless, the whole ATR prism coupler does not need to be so, but a part of the ATR prism coupler should just become a medium with a larger refractive index than the refractive index of the analyte.

Furthermore, a word "near" in this specification points out a general near field area, and is used in the meaning of pointing out a space domain comparable to or not more than a wavelength of an electromagnetic wave used in the sensor device in this specification.

EXAMPLE 1

Figure 5:
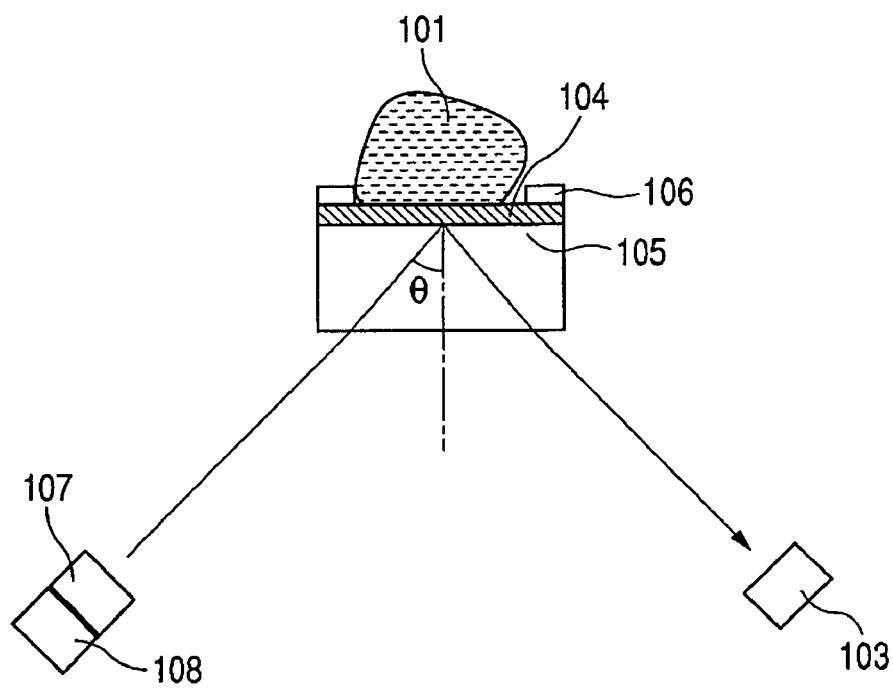
FIG. 5 is a sectional view showing structure of a sensor device according to a first example.

FIG. 5 is a sectional view showing an example of structure of a sensor device according to the present invention. In FIG. 5, reference numeral 105 denotes an ATR prism coupler, 104 denotes a semiconductor, and 101 denotes an analyte. At the time of such locatement (this is called Kretschmann geometoryKretschmann geometery) as that in FIG. 5, the semiconductor 104 must be a thinness not more than a wavelength, and typically, it is selected from among about $\lambda/50$ to $\lambda/10$. More preferably, it is desirable to analyze the thickness of the semiconductor 104 and to perform an optimal design.

For example, when analyzing three-layer structure of an ATR prism coupler/a semiconductor/an analyte using a Fresnel's reflection formula, it is possible to determine an optimum value of the thickness of the semiconductor 104. This method is a method known well by those skilled in the art. In Kretschmann geometry of a first example as shown in FIG. 5, when an optimal design to the semiconductor 104 is made, reflective strength in the case of satisfying resonance conditions approaches zero without limit in result of the angular interrogation or carrier density interrogation, and measurement becomes easy. In addition, reference numeral 108 denotes angle change means of an incident wave and reference numeral 106 denotes carrier density change means of a semiconductor, and they are for performing angular interrogation and carrier density interrogation, respectively. In addition, reference numeral 103 denotes a detector. There is no restriction in respect of locatement of an analyte in such Kretschmann geometery.

The following is a numerical example of the first example. For example, when a frequency of an electromagnetic wave to be used is set at 3.0 [THz], since transparency is extremely high when high resistivity Si (specific resistance 10 [kΩ·cm] or more) is used for the ATR prism coupler 105, it is not necessary to consider attenuation. It is assumed that an adequate substance is used for the analyte 101, and values are $n_p$=3.4 and $n_a$=2.55. Furthermore, as a semiconductor material, Si (N=1.0×10$^{18}$ [cm$^{-3}$], $m_{eff}$=0.4, $\gamma/2\pi$=1.4 [THz], $\in_b$=11.6) is assumed in consideration of ease of manufacturing. At this time, when a Fresnel's reflection formula is used, an optimum thickness of Si is 2.5 [μm]. When numerical analysis is advanced under the above assumption, it is shown that sensitivity S(pθ) is 34 [deg/RIU], and it will be able to be said that this value is almost comparable sensitivity to typical sensitivity of surface plasmon resonance sensors in a visible region.

In addition, a production procedure of structure according to the first example will be explained below. A high resistivity Si substrate is used as the ATR prism coupler 105. As for the semiconductor 104, for example, n-Si is epitaxially grown on the high resistivity Si substrate using thermal CVD or the like. In the above-mentioned numerical example, electrons are selected as carriers and it is made to be free electron density of 1.0×10$^{18}$ [cm$^{-3}$] and a film thickness of 2.5 [μm]. The analyte 101 may be just placed on the semiconductor 104, and when doing in this way, it is possible to construct comparatively easily the Kretschmann geometery as shown in FIG. 5. In addition, a method of rotating and using a reflective mirror or rotating the sensor device itself is simplest as the angle change means 108, In addition, when using electrodes as carrier density modification means 106, it is possible to select a method of adding a plurality of electrodes on a surface of the semiconductor 104 using semiconductor process, and applying an electric field for control on the semiconductor surface.

EXAMPLE 2

Figure 6:
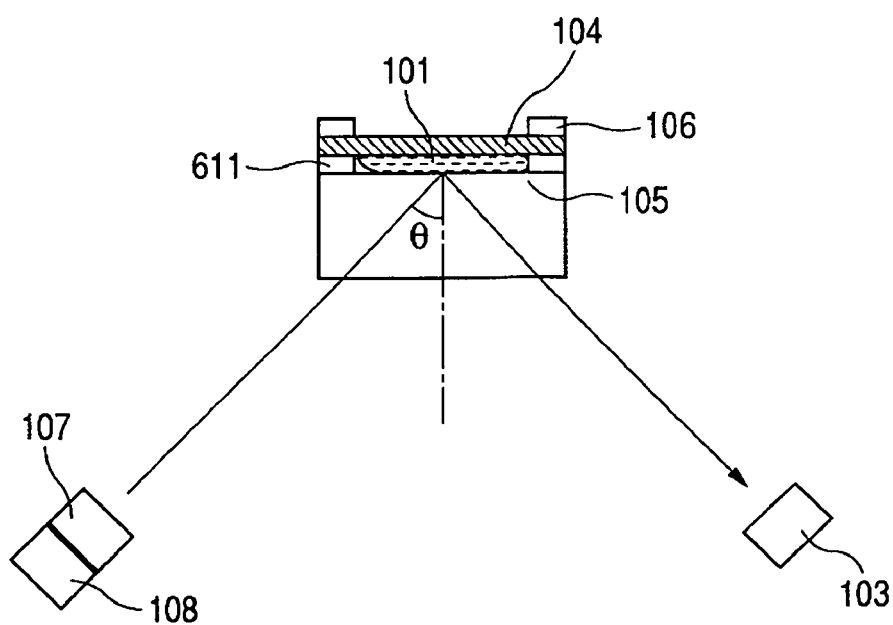
FIG. 6 is a sectional view showing structure of a sensor device according to a second example.

FIG. 6 is a sectional view showing an example of structure of a sensor device according to the present invention. In FIG. 6, reference numeral 105 denotes the ATR prism coupler, 104 denotes the semiconductor, and 101 denotes the analyte. At the time of such locatement (this is called Otto geometry) as that in FIG. 6, there arises a restriction in a depth direction of the analyte 101. This is because the semiconductor 104 needs to be located near the ATR prism coupler 105 as already described. Typically, it is selected from among about $\lambda/250$ to $\lambda/50$. More preferably, it is desirable to analyze beforehand an optimum thickness of a spacer 611 for locating the analyte 101, and to perform an optimal design. For example, an optimum value of the thickness of the spacer 611 is determined using the Fresnel's reflection formula. When an optimal design is made in this way, reflective strength in the case of satisfying resonance conditions approaches zero without limit in result of the angular interrogation or carrier density interrogation, and measurement becomes easy. In addition, reference numeral 108 denotes angle change means of an incident wave and reference numeral 106 denotes carrier density change means of a semiconductor, and they are for performing angular interrogation and carrier density interrogation, respectively. Furthermore, reference numeral 103 denotes a detector. Even in such locatement (Otto geometry) seldom liked in the visible region, since a wavelength from a millimeter wave band to a terahertz band is different in order from it in a visible region, it is an advantage different from the past that restrictions for locating the analyte 104 are comparatively few.

The following is a numerical example of a second example. In the Otto geometory, since manufacturing is easy in comparison with the Kretschmann geometry, it is also good to select a semiconductor material which has comparatively high mobility as follows. That is, high resistivity Si is used for the ATR prism coupler 105, and with assuming an adequate substance as the analyte 101, values are set at $n_p=3.4$, and $n_a=2.55$. Furthermore, as a semiconductor material to be used, InAs ($n=1.0\times10^{16}$ [cm$^{-3}$], $m_{eff}=0.03$, $\gamma/2\pi=0.30$ [THz], $\in_b=14.5$) is assumed in consideration of largeness of mobility. When numerical analysis is advanced under the above assumption, for example, when a frequency of an electromagnetic wave to be used is set at 1.0 [THz], it is shown that the sensitivity $S(p\theta)$ is 44 [deg/RIU].

A production procedure of structure according to the second example will be explained below. A high resistivity Si substrate is used as the ATR prism coupler 105. As for the semiconductor 104, for example, it is sufficient to use an InAs single-crystal substrate in the above-mentioned numerical example, or to grow InAs epitaxially on a certain substrate. The ATR prism coupler 105 and semiconductor 104 are bonded through a spacer 611. In this way, it is possible to construct comparatively easily the Otto geometry as shown in FIG. 6. In addition, when the analyte is liquid or gaseous, a gap formed by the spacer 611, ATR prism coupler 105, and semiconductor 104 may become a guide (pass) for guiding the analyte 101. As mentioned above, a method of rotating and using a reflective mirror or rotating the sensor device itself is simplest as the angle change means 108. In addition, when using electrodes as carrier density modification means 106, it is possible to select a method of adding a plurality of electrodes on a surface of the semiconductor 104 using semiconductor process, and applying an electric field for control on the semiconductor surface.

EXAMPLE 3

Figure 7:
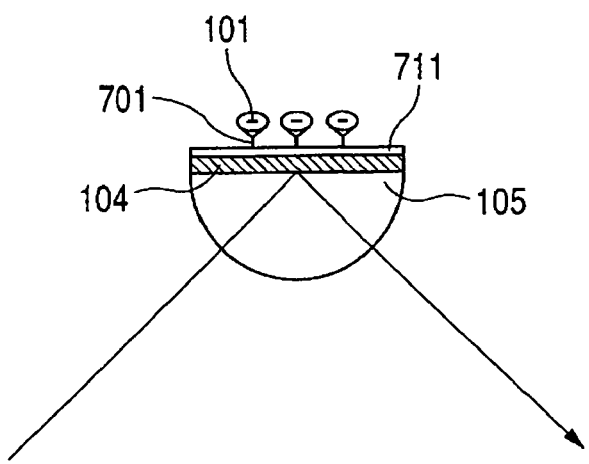
FIG. 7 is a sectional view showing structure of a sensor device according to a third example.

FIG. 7 is a sectional view showing an example of structure of a sensor device according to the present invention. Example 3 is a modified example of the first example, and shows an application method as a biosensor in the case that an analyte is an antigen in an antigen-antibody reaction. In FIG. 7, reference numeral 105 denotes the ATR prism coupler, 104 denotes the semiconductor, and 101 denotes an antigen in an antigen-antibody reaction, that is, an analyte. In addition, reference numeral 711 denotes adsorptive coating and 701 denotes an antibody. At this time, it is also sufficient to use a gold film, known for adsorptiveness being high, as the adsorptive coating 711. Nevertheless, since the gold film needs to have high transparency at a wavelength to be used, for example, when a frequency near 1 [THz] is selected as the electromagnetic wave to be used, transparency is secured by making a film thickness not more than 5 [nm]. Thus, an antibody 701 is held on the adsorptive coating 711, and when the antigen 101 reacts on the antibody 701, a state of surface plasmon held by the semiconductor 104 changes for a resonance condition in an angular interrogation or a carrier density interrogation to shift.

As such a biosensor, various applications are possible, for example, examination of a reaction of constructing a double strand by hybridization of DNA, examination of a reaction of ligands, such as protein, peptide, and amino acid, and a receptor, examination of a reaction of sugar chain coupling.

As a production procedure of structure according to a third example, it is possible to use the method in the first example having almost equal structure, and furthermore, it is possible to add easily the gold film as the adsorptive coating 711 using typical semiconductor process technology. As a method of fixing the antibody 701 to the adsorptive coating 711, it is possible to select a method of selecting the antibody 701 which has a functional group with high affinity with gold, and dropping it with a spotter or the like by making it into a solution, for example.

EXAMPLE 4

Figure 8A:
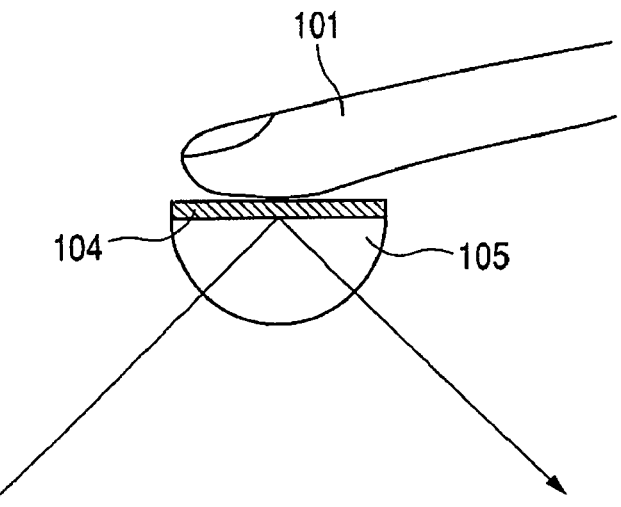
FIGS. 8A and 8B are drawings in the cases of using structure of a sensor device according to a fourth example for a medical examination and a food evaluation.
Figure 8B:
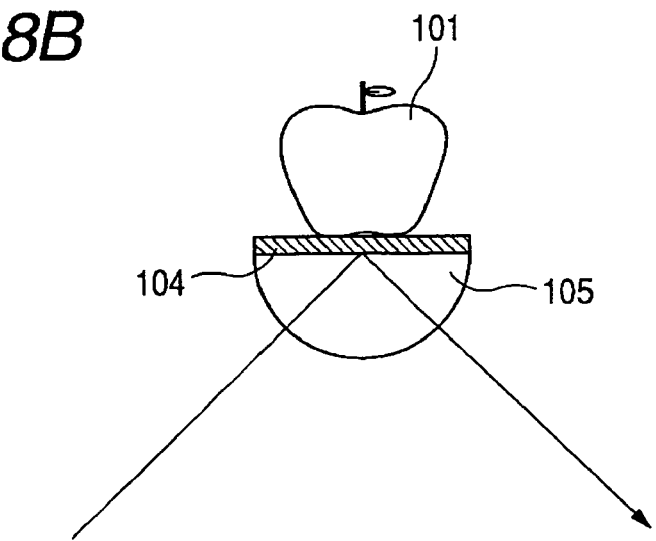

FIGS. 8A and 8B are drawings showing such locatement that can perform a medical examination or a food evaluation with a sensor device according to the present invention. A fourth example is a modified example of the first example, and in FIGS. 8A and 8B, reference numeral 105 denotes the ATR prism coupler, and 104 denotes the semiconductor. Since the surface plasmon held by the semiconductor 104 reaches a space domain comparative to a wavelength of the electromagnetic wave to be used, it is possible to select, for example, a human being's hand, face, or the like as the analyte 101, and also to measure a tela subcutanea nondestructively (FIG. 8A). When a wavelength to be used is a frequency region of a millimeter wave band to a terahertz wave band, since a part in order of a subcutaneous depth of 10 [mm] to 10 [μm] is measured, it is expectable to be able to measure a state of dermis including collagen, a sudoriferous gland, and a blood capillary to high sensitivity, for example, there is a possibility as a sensor of checking a health condition without collecting blood by performing blood glucose level measurement in a hypodermic blood capillary. Alternatively, it is possible to select a fruit as the analyte 101 and to measure internal fabric nondestructively (FIG. 8B). When a similar frequency region is selected, it is expectable to be able to measure a state of fruity flesh to high sensitivity, for example, there is a possibility as a sensor of checking a food state without giving a scratch by performing fruit sugar density measurement in fruity flesh under a peel.

Since it is possible to control the free carrier concentration of a semiconductor as explained above, it is possible to enhance the sensitivity according to a wavelength of an electromagnetic wave to be used. Using such structure, it becomes also possible in a millimeter wave band to a terahertz band to perform such measurement of optical properties of an analyte with high sensitivity that has been already performed in a visible region. In addition, it is also possible to perform measurement different from the conventional as a sensing operation by controlling free carrier density in a semiconductor.

This application claims priority from Japanese Patent Application No. 2005-256654 filed on Sep. 5, 2005, which is hereby incorporated by reference herein.

The invention claimed is:

1. A sensor device comprising:
   an analyte holding portion for locating an analyte;
   a radiation means for radiating an electromagnetic wave which includes a part of a frequency region from 30 GHz to 30 THz toward the analyte holding portion; and
   a detection means for detecting the electromagnetic wave reflected from the analyte holding portion,
   the analyte holding portion comprising a semiconductor and a medium, a real part of a dielectric constant of the semiconductor being negative, the square of a refractive index of the medium being smaller than the absolute value of the real part of the dielectric constant, the analyte opposing the medium via the semiconductor when detecting the analyte.

2. The sensor device according to claim 1, wherein the analyte holding portion comprises an electrode.

3. The sensor device according to claim 2, wherein the electrode is a means of applying an electric field to the semiconductor.

4. The sensor device according to claim 1 which comprises a light radiation means for radiating light on the semiconductor.

5. The sensor device according to claim 1 which comprises an incident angle change means for changing an incident angle of an electromagnetic wave which includes a part of a frequency region from 30 GHz to 30 THz to the analyte holding portion.

6. The sensor device according to claim 1, wherein the semiconductor is selected from the group consisting of InAs, GaAs, InSb and InN.

7. The sensor device according to claim 1, wherein the analyte holding portion is coated with a gold film 5 nm or less in thickness so as to improve an adsorptiveness of an analyte.

8. The sensor device according to claim 1, wherein a carrier density of the semiconductor is in a range from not less than $10^{15}$ cm$^{-3}$ to not more than $10^{19}$ cm$^{-3}$.

9. A sensor device comprising:

an analyte holding portion for locating an analyte;

a radiation means for radiating an electromagnetic wave which includes a part of a frequency region from 30 GHz to 30 THz toward the analyte holding portion; and a detection means for detecting the electromagnetic wave reflected from the analyte holding portion, the analyte holding portion comprising a semiconductor and a medium, a real part of a dielectric constant of the semiconductor being negative, the square of a refractive index of the medium being smaller than the absolute value of the real part of the dielectric constant, the analyte being located between the semiconductor and the medium when detecting the analyte.

10. The sensor device according to claim 9, wherein the analyte holding portion comprises an electrode.

11. The sensor device according to claim 10, wherein the electrode is a means of applying an electric field to the semiconductor.

12. The sensor device according to claim 9 which comprises a light radiation means for radiating light on the semiconductor.

13. The sensor device according to claim 9 which comprises an incident angle change means for changing an incident angle of an electromagnetic wave which includes a part of a frequency region from 30 GHz to 30 THz to the analyte holding portion.

14. The sensor device according to claim 9, wherein the semiconductor is selected from the group consisting of InAs, GaAs, InSb and In.

15. The sensor device according to claim 9, wherein the analyte holding portion is coated with a gold film 5 nm or less in thickness so as to improve an adsorptiveness of an analyte.

16. The sensor device according to claim 9, wherein a carrier density of the semiconductor is in a range from not less than $10^{15}$ cm$^{-3}$ to not more than $10^{19}$ cm$^{-3}$.

17. A sensor device comprising:

an analyte holding portion for locating an analyte;

a radiation means for radiating an electromagnetic wave which includes a part of a frequency region from 30 GHz to 30 THz toward the analyte holding portion; and a detection means for detecting the electromagnetic wave reflected from the analyte holding portion, the analyte holding portion comprising a first layer and a second layer, the first layer and second layer satisfying the following formula:

$$Re(\epsilon_1) < -n_2^2$$

where $Re(\epsilon_1)$ is a real part of a dielectric constant of the first layer, and $n_2$ is a refractive index of the second layer.

* * * * *